United States Patent [19] [11] 4,162,939
Yoshikumi et al. [45] Jul. 31, 1979

[54] METHOD FOR THE CULTIVATION OF BASIDIOMYCETES BELONGING TO THE GENUS CORIOLUS OF POLYPORACEAE

[75] Inventors: Chikao Yoshikumi, Kunitachi; Takao Furusho, Tokyo; Kenichi Matsunaga; Noriyuki Toyoda, both of Hino, all of Japan

[73] Assignee: Kureha Kagaku Kogyo Kabushiki Kaisha, Tokyo, Japan

[21] Appl. No.: 824,117

[22] Filed: Aug. 12, 1977

[30] Foreign Application Priority Data

Aug. 30, 1976 [JP] Japan .................. 51-102628

[51] Int. Cl.² .................. C12D 13/04; C12B 1/08; C12B 3/12
[52] U.S. Cl. .................. 435/254; 435/101; 435/911
[58] Field of Search .................. 195/31 P, 81, 100

[56] References Cited

U.S. PATENT DOCUMENTS

| | | | |
|---|---|---|---|
| 3,301,848 | 1/1967 | Halleck | 536/1 |
| 3,759,896 | 9/1973 | Komatsu et al. | 536/1 |
| 3,822,250 | 7/1974 | Kimura et al. | 536/1 |
| 3,960,832 | 6/1976 | Kang et al. | 536/1 |
| 4,051,314 | 9/1977 | Ohtsuka et al. | 536/1 |

OTHER PUBLICATIONS

Wolpert, "Studies in the Physiology of the Fungi", *Ann. Mo. Bot. Gard.*, vol. 11, (1924), pp. 43-96.
Neijssel et al., "The Regulation of Carbohydrate Metabolism in *Klebsiella aerogenes* NCTC 418 Organisms, Growing in Chemostat Culture", *Arch. Microbiol.* vol. 106, (1975), pp. 251-258.

*Primary Examiner*—Thomas G. Wiseman
*Attorney, Agent, or Firm*—Stevens, Davis, Miller & Mosher

[57] ABSTRACT

The Basidiomycetes belonging to the genus Coriolus of family Polyporaceae are cultivated by using a glucose-yeast extract medium with the mixed ratio of glucose to yeast extract being within a specified range to improve the yield of mycelia obtained by the cultivation.

4 Claims, No Drawings

METHOD FOR THE CULTIVATION OF BASIDIOMYCETES BELONGING TO THE GENUS CORIOLUS OF POLYPORACEAE

BACKGROUND OF THE INVENTION

This invention relates to a method for the cultivation of the Basidiomycetes belonging to the genus Coriolus of family Polyporaceae, and more particularly to a cultivation method for improving the yield of the mycelia of the Basidiomycetes by using a glucose-yeast extract medium of a specific composition.

The polysaccharides obtained from the Basidiomycetes belonging to the genus Coriolus of Polyporaceae have come to attract public attention in recent years for their excellent anti-tumour activity and other pharmacological effects, and demands have been raised for development of means for realizing advantageous industrial production of such substances, or more specifically, provision of a high-yield cultivation method of the Basidiomycetes.

We have studied a cultivation method capable of propagating the Basidiomycetes belonging to the genus Coriolus of Polyporaceae in a high yield, and as a result, have reached a finding that the yield of the mycelia of the Basidiomycetes is markedly improved when the fungi are cultivated by using a glucose-yeast extract medium containing glucose and yeast extract in high concentrations and in a specific ratio.

Heretofore, for cultivation of the Basidiomycetes, there has been generally employed a medium of the type ordinarily used for cultivation of microorganism, and no attempts has ever been made to use a glucose-yeast extract medium of a specific composition for cultivation of the Basidiomycetes.

BRIEF SUMMARY OF THE INVENTION

The salient feature of this invention resides in use of a glucose-yeast extract medium containing glucose and yeast extract in a ratio of 3 to 15:1, with the glucose in the medium being 7.5 to 15%, for cultivation of the Basidiomycetes belonging to the genus Coriolus of Polyporaceae.

An object of this invention, therefore, is to provide a method for cultivation of the Basidiomycetes belonging to the genus Coriolus of Polyporaceae, the method being capable of significantly increasing the yield of mycelia by using the above medium.

Other objects of this invention will become apparent from reviewing the following detailed description of the invention.

DETAILED DESCRIPTION OF THE INVENTION

The present invention, as stated above, is intended to cultivate the Basidiomycetes belonging to the genus Coriolus of Polyporaceae by using a glucose-yeast extract medium where the ratio of glucose to yeast extract is 3 to 15:1 and the glucose content is within the range of 7.5 to 15% by weight. It is to be noted that even if the ratio of glucose to yeast extract in the medium composition is within the range of 3 to 15:1, no appreciable increase of mycelia yield is expected when the glucose content in the medium is lower than 7.5%. Also, the yield is little changed even if the glucose content exceeds 15%, so that use of glucose in excess of 15% is not expedient economically. When a Basidiomycete belonging to the genus Coriolus is cultivated by using a glucose-yeast extract medium of a specified composition such as above-mentioned according to this invention, there is obtained 2 to 5 times as high a yield of mycelia as when such Basidiomycete is cultivated by using conventional media, for example natural media such as peptone medium or its modified form, malt extract medium, corn extract medium or corn steep liquor medium, or synthetic media such as Pfeffer's medium, Sabouraud's medium or Meyer's medium. Also, the method of this invention provides 2 to 4 times as high yield of mycelia as when using any one of the glucose-yeast extract media having a composition outside of the specified range of this invention. Regarding the composition of the glucose-yeast extract medium used in this invention, it is most preferable for providing the highest yield to use a medium where the glucose content is within the range of 10 to 15% and the glucose/yeast extract ratio is within the range of 6 to 10:1.

The medium used in this invention may be supplemented with a mineral material selected from phosphorus, manganese, magnesium, calcium, iron and the like in the form of a salt, as well as nutrients such as vitamins.

As for the culturing conditions employed in this invention, cultivation is practiced generally at a temperature of 25°±3° C. for a period of 3 to 10 days in the case of submerged culture with aeration and agitation and 20 to 30 days in the case of stationary culture.

The Basidiomycetes belonging to the genus Coriolus of Polyporaceae used in this invention are all known in the art, and their mycological properties are described in "COLORED ILLUSTRATION OF FUNGI OF JAPAN" by Rokuya Imazeki and Tsuguo Hongo, Vols, I, 1975, and II, 1974. Of these Basidiomycetes, the following species are deposited in the Fermentation Research Institute, Agency of Industrial Science and Technology (Chiba-shi, Japan), of the Japanese Government:

| Species | Deposit No. | Deposit Date |
| --- | --- | --- |
| Coriolus versicolor (Fr.) Quel. CM-103 | FERM-P No. 2414 | Dec. 25, 1973 |
| Coriolus consors (Berk.) Imaz. CM-166 | FERM-P No. 988 | Jun. 24, 1971 |
| Coriolus hirsutus (Fr.) Quel. CM-151 | FERM-P No. 2711 | Sept. 6, 1974 |
| Coriolus pargamenus (Fr.) Pat. CM-161 | FERM-P No. 2712 | Sept. 6, 1974 |

Of these Basidiomycetes, the use of Coriolus versicolor (Fr.) Quel. is most preferred.

The mycelia obtained by cultivating any of the above-mentioned Basidiomycetes belonging to the genus Coriolus are extracted with an aqueous solvent such as water or dilute alkaline solution, and the obtained extract solution is refined to eliminate the low-molecular weight fraction and the residue is further dried, thereby obtaining a substance composed of polysaccharide. The thus obtained polysaccharide contains nitrogen in its molecules and has an excellent anti-tumour activity. This substance, when administered to mice, exhibits an excellent anti-tumour activity not only its intraperitoneal administration but also in oral administration. Many reports have already been published on the anti-tumour activity of this substance. The use of this substance is not limited to such anti-tumour applications; the results of the tests revealed its excellent effect for recovery of immunity by the host, prevention of the side effects in chemotherapy, and prevention of decline of the patient's physical condition after an operation or other events. It was also noted in the tests that oral administration of this substance has effect in increasing appetite, curing intestinal disorders and promoting urination.

The invention is now described in further detail by way of example, but obviously, the scope of this invention is not limited to the following embodiment. Percent (%) used in the following description of Example is by weight.

EXAMPLE 20 ml portions of each of the media having the compositions shown in Table 1 were each put into 100-ml conical flasks, and each of these media was inoculated with a seed culture of Coriolus versicolor (Fr.) Quel. Cm-103 (FERM-P No. 2414) and subjected to stationary culture at 25° to 28° C. for 28 days. After completion of cultivation, the yield of mycelia produced in each flask was determined, obtaining the results shown in Table 1. Also shown in Table 1 are the results of the comparative examples where cultivation was performed under the same conditions as described above except for use of the glucose-yeast extract media of compositions outside of the specified range of this invention.

Table 1

| Glucose (%) | Yeast extract (%) | Glucose/yeast extract | Yield of mycelia (g/l) |
|---|---|---|---|
| This Invention | | | |
| 15 | 1.0 | 15 | 28.7 |
| 15 | 1.25 | 12 | 33.0 |
| 15 | 1.5 | 10 | 39.1 |
| 12.5 | 1.0 | 12.5 | 34.2 |

Table 1-continued

| Glucose (%) | Yeast extract (%) | Glucose/yeast extract | Yield of mycelia (g/l) |
|---|---|---|---|
| 12.5 | 1.25 | 10 | 39.2 |
| 12.5 | 1.5 | 8.3 | 42.9 |
| 10.0 | 0.75 | 13.3 | 30.7 |
| 10.0 | 1.0 | 10 | 35.4 |
| 10.0 | 1.25 | 8.0 | 41.2 |
| 10.0 | 1.5 | 6.7 | 40.6 |
| 7.5 | 0.5 | 15 | 27.6 |
| 7.5 | 0.75 | 10 | 33.7 |
| 7.5 | 1.0 | 7.5 | 32.2 |
| 7.5 | 1.25 | 6 | 30.3 |
| Comparative examples | | | |
| 2.5 | 0.25 | 10 | 11.0 |
| 5.0 | 0.5 | 10 | 23.3 |
| 7.5 | 0.25 | 30 | 18.8 |
| 10.0 | 0.5 | 20 | 23.1 |
| 12.5 | 0.5 | 25 | 15.9 |
| 15.0 | 0.75 | 20 | 22.8 |
| 2.5 | 1.25 | 2 | 5.8 |

It will be understood from the above table that the yield of the mycelia obtained from cultivation according to the method of this invention is markedly improved over the comparative examples.

What is claimed is:

1. In a method of cultivation of a Basidiomycete belonging to the genus Coriolus comprising cultivating said Basidiomycete in a synthetic culture medium at a temperature of 25°±3° C., under stationary or submerged conditions, the wherein improvement comprises:
   cultivating said Basidiomycete in a glucose-yeast extract culture medium consisting of 7.5 to 15% by weight of glucose, yeast extract and water, with the weight ratio of glucose to yeast extract being 3:1 to 15:1.

2. The cultivation method according to claim 1, wherein the glucose to yeast extract ratio is 6 to 10:1.

3. The cultivation method according to claim 1, wherein the glucose content in the medium is within the range of 10 to 15% by weight.

4. The cultivation method according to claim 1, wherein said Basidiomycete is Coriolus versicolor (Fr.) Quel.

* * * * *